United States Patent
Olazaran et al.

US006342375B1

(10) Patent No.: US 6,342,375 B1
(45) Date of Patent: Jan. 29, 2002

(54) **MODIFIED METHYLOTROPHIC *PICHIA PASTORIS* YEAST WHICH SECRETES HUMAN GROWTH HORMONE**

(75) Inventors: Martha Guerrero Olazaran; Hugo Barrera Saldana; Jose Maria Viader Salvado, all of Monterrey Nuevo Leon (MX)

(73) Assignee: Universidad Autonoma de Nuevo Leon (MX)

( * ) Notice: Subject to any disclaimer, the term of this patent is extended or adjusted under 35 U.S.C. 154(b) by 0 days.

(21) Appl. No.: 09/284,878

(22) PCT Filed: Oct. 24, 1997

(86) PCT No.: PCT/MX97/00033

§ 371 Date: Jul. 21, 1999

§ 102(e) Date: Jul. 21, 1999

(87) PCT Pub. No.: WO98/20035

PCT Pub. Date: May 14, 1998

(30) Foreign Application Priority Data

Oct. 24, 1996 (MX) .............................................. 965082

(51) Int. Cl.[7] ............................ C12P 21/00; C12N 1/14; C12N 15/74; C07H 21/04
(52) U.S. Cl. .................. 435/69.4; 435/255.5; 435/483; 536/23.1; 536/24.1; 536/24.3
(58) Field of Search ............................ 435/69.4, 255.5, 435/483; 536/23.1, 24.1, 24.3

(56) References Cited

U.S. PATENT DOCUMENTS

| | | |
|---|---|---|
| 4,342,832 A | 8/1982 | Goeddel et al. |
| 4,683,293 A | 7/1987 | Craig |
| 4,808,537 A | 2/1989 | Stroman et al. |
| 4,812,405 A | 3/1989 | Lair et al. |
| 4,818,700 A | 4/1989 | Cregg et al. |
| 4,837,148 A | 6/1989 | Cregg |
| 4,855,231 A | 8/1989 | Stroman et al. |
| 4,857,467 A | 8/1989 | Sreekrishna et al. |
| 4,879,231 A | 11/1989 | Stroman et al. |
| 4,882,279 A | 11/1989 | Cregg |
| 4,885,242 A | 12/1989 | Cregg |
| 4,929,555 A | 5/1990 | Cregg et al. |
| 5,002,876 A | 3/1991 | Sreekrishna et al. |
| 5,004,688 A | 4/1991 | Craig et al. |
| 5,032,516 A | 7/1991 | Cregg |
| 5,102,789 A | 4/1992 | Siegel et al. |
| 5,122,465 A | 6/1992 | Cregg et al. |
| 5,166,329 A | 11/1992 | Cregg |
| 5,268,273 A | 12/1993 | Buckholz |
| 5,324,639 A | * 6/1994 | Brierly et al. .............. 435/69.4 |
| 5,330,901 A | 7/1994 | Prevatt et al. |
| 5,670,630 A | 9/1997 | Thill |
| 5,707,828 A | 1/1998 | Sreekrishna et al. |
| 5,827,684 A | 10/1998 | Sreekrishna et al. |
| 5,856,123 A | 1/1999 | Hitzeman et al. |
| 6,107,057 A | 8/2000 | Crawford et al. |

FOREIGN PATENT DOCUMENTS

| | | |
|---|---|---|
| EP | 0 127 305 A1 | 12/1984 |
| EP | 0 306 673 A1 | 3/1989 |
| EP | 0 344 459 | 12/1989 |
| WO | WO 00/01829 | 1/2000 |

OTHER PUBLICATIONS

Aprikyan et al. Expression and secretion of human grwoth hormome in the methylotrophic yeast *Hansenula polymorpha*. Doki Akad Nauk SSSR. vol. 321(2):390–394, Feb. 1991.*

Brankamp, R.G. et al., "Expression of a Synthetic Gene Encoding the Anticoagulant–Antimetastatic Protein Ghilanten by the Methylotropic Yeast *Pichia pastoris*," *Protein Expression and Purification* 6:813–820 (1995), Academic Press, Inc.

International Search Report for International Application No. PCT/MX97/00033, mailed Apr. 13, 1998.

* cited by examiner

*Primary Examiner*—Terry McKelvey
*Assistant Examiner*—William Sandals
(74) *Attorney, Agent, or Firm*—Sterne, Kessler, Goldstein & Fox P.L.L.C.

(57) ABSTRACT

In the present system an adequate expression system for the production and secretion of biologically active human growth hormone (HGH) in its natural form in which a methylotrophic yeast such as *Pichia pastoris* is used as host organism has been developed. This invention includes a methylotrophic yeast transformed with at least one copy of a functional cDNA sequence encoding HGH, which is functionally associated with a second DNA sequence encoding the *S. cerevisae* alpha factor pre-pro sequence (including the proteolytic processing site: lys-arg), and in which both DNA sequences are under the regulation of a methylotrophic yeast gene promoter which is inducible with methanol. Methylotrophic yeasts containing in their genome at least one copy of the DNA sequence efficiently produce and secrete mature, correctly processes and biologically active HGH, into the culture medium.

24 Claims, 2 Drawing Sheets

MODIFIED METHYLOTROPHIC *PICHIA PASTORIS* YEAST WHICH SECRETES HUMAN GROWTH HORMONE

TECHNICAL FIELD OF THE INVENTION

The present invention is related to the biopharmaceutical area, in particular to the production of the human growth hormone (HGH) that has been successfully used in treating different health problems. Specifically speaking, it is related to the use of recombinant DNA technology for the production of recombinant human growth hormone (rHGH) in methylotrophic yeast transformed with the cDNA sequence of mature HGH and the *S. Cerevisiae* alpha-mating factor pre-pro sequence which, under the regulation of a methanol inducible promoter region of a methylotrophic yeast gene and grown under certain conditions, permit the expression and secretion of rHGH towards the culture medium. The invention further relates to said methylotrophic yeast, the DNA fragments and the vectors used in said transformation.

BACKGROUND TO THE INVENTION

The problems in which HGH is currently used as a part of therapy are: the treatment of pituitary dwarfism (caused by malfunctioning of the hypophysis); removal of fatty acids and hence the treatment of obesity; improvement of vascularization; promotion of muscle mass gain in elderly people; the treatment of ulcers and bone fractures, and the acceleration of the regeneration of damaged tissues.

Human growth hormone (HGH) or somatotropin is a globular polypeptide of 191 amino acids without sugar residues, with a molecular weight of approximately 22 kDa. Taking into account the three dimensional model of the pig growth hormone, HGH is considered to be made up of 4 antiparallel alpha helices. The molecule has two disulfide bonds that connect helix 4 with the carboxyl terminal end of the protein and helix 1 with helix 4 (Devos et al., 1992).

The production of HGH in the hypophysis is episodical and is governed by the action of two hypothalamic hormones, the growth hormone releasing factor and somatostatin. While the former stimulates its synthesis, the later inhibits its release. The hormone acts directly on the target tissue cells, or by means of intermediaries of hormonal type called somatomedins (Daughaday, 1985). The catabolic effects of HGH include: increase in lipolysis, oxidation of fatty acids and decreased transportation of glucose, with a consequent increase in the concentration of glucose in the blood (Daughaday, 1985). The anabolic effects include: increase in the transportation of amino acids with a decrease in their catabolism and stimulation of the synthesis of DNA, RNA and proteins in the liver (Campbell, 1988). In general terms, the net effect of HGH and of somatomedins is considered to be anabolic (Welsh, 1985). Among the important functions of HGH is its role in post-natal growth.

The importance of HGH and its application in the biopharmaceutical area is reflected in the uses it has had: it has been used successfully in the treatment of pituitary dwarfism; it removes fatty acids and is therefore used in the treatment of obesity; it improves vascularization and promotes muscle mass gain in the elderly; it is used in the treatment of ulcers and bone fractures and accelerate the regeneration of damaged tissues (Watson, 1991).

Recombinant HGH was synthesised for the time in *Escherichia coli* (*E. coli*) (2.4 mg/L of culture medium) by Goeddel and coworkers in 1979 under the control of the lac promoter (Goeddel et al., 1979). Secretion of the hormone into the periplasm of the bacteria was achieved by Gray and coworkers in 1985 whose strategy consisted of using the cDNA of HGH fused to the region encoding the signal peptide of the alkaline phosphatase gene to *E. coli*, making it possible to produce 0.28 mg/L of the hormone, 82% of which was directed to the periplasmic space (Gray, et al., 1985). Becker and Hsiung in 1986 achieved a concentration of 15 mg/L of HGH in the periplasmic space thanks to the outer membrane protein (OMP) peptide signal of *E. coli*. In 1987, Chang et al. fused the cDNA of HGH to the region encoding the enterotoxin II signal peptide of *E. coli* using the alkaline phosphatase promoter of this same bacterium produced 15.4 mg/L of HGH, 90% of which was exported to the periplasm. Kato et al., in 1987, reported the synthesis of HGH and its secretion into the culture medium, using a plasmid carrying both the HGH hybrid and the kill genes. The kill gene expresses a protein that permeabilized the outer membrane. The HGH concentration reached was 20.5 mg/L of which 11.2 mg/L were secreted into the medium and 8.6 mg/L remained in the periplasm. Hsiung et al., in 1989, used the bacteriocin releasing protein to allow recombinant HGH, which had been secreted into the periplasm thanks to the presence of the OMP signal peptide, to be released into the culture medium with a concentration of up to 69.6 mg/L. In addition to the *E. coli*, recombinant HGH has also been produced in *B. subtilis*, *S. cerevisiae* and mammalian cells. However, recombinant HGH synthesis in mammalian cells has given very low yields (in the order of $\mu$g/L) (Ortiz-López, 1992; and Pavlakis et al., 1991).

Yeast offer advantages over bacteria in heterologous protein production because, although they are unicellular organisms easy to manipulate and grow quickly, their cellular organization is eukaryotic, making it possible to perform expression and maturation processes characteristic of animal and plant cells. Moreover they can secrete recombinant proteins into the culture medium, being recombinant product levels higher there than in the cytoplasm. Evenmore, the secreted products are obtained with a high degree of purity (since few endogenous proteins are secreted) and therefore the purification steps are reduced. Finally, they offer a suitable environment for the adequate folding of proteins, especially of those that contain disulfide bonds.

*Pichia pastoris* is a yeast that can metabolize methanol as the sole source of carbon and energy (methylotrophic) and is currently used for the production of recombinant proteins since as a production system it is simpler, cheaper and more productive than other higher eukaryotic systems. Being a yeast, it shares the advantages of easy genetic and biochemical manipulation of *S. cerevisiae* but surpasses its heterologous protein production levels (10 to 100 times greater) (Cregg et al., 1993; and Romanos, 1995). Furthermore, expression systems have been developed in *P. pastoris* that overcome the problems associated with *S. cerevisiae*, such as how to increase the number of copies of the heterologous gene and genetic stability on scaling up. This system is characterized by the use of a promoter that controls the expression of the heterologous gene. This promoter is derived from a yeast gene that can be induced with methanol and that is subject to precise regulation, often leading to high levels of heterologous gene expression.

*P. pastoris* has been used in the production of several heterologous proteins, for example the hepatitis B surface antigen (Cregg, et al., 1987), Iysozyme and invertase (Digan, 1988; Tschopp, 1987), tumour necrosis factor (Sreekrishna, 1989), among others. However, efforts to produce other products from heterologous genes in *Pichia pastoris*, especially via secretion, have given variable results, and there are examples of low yields, proteolysis of the secreted protein, inefficient secretion and in some cases the protein product has not been detected (Romanos, 1995). With the studies done to date in this respect, it is difficult to predict whether one protein in particular will be synthesized and/or secreted by a methylotrophic yeast or if this yeast will tolerate the presence of the produced heterologous protein; likewise, it is also difficult to predict if these processes will be efficient.

Considering 1) that the production levels of a recombinant protein in cultures at flask level do not accurately reflect the production levels observed at the fermenter level; 2) that according to the literature on *P. pastoris*, these levels rise considerably when *P. pastoris* is grown on a large scale; 3) the availability of technology for fermentation at high cell densities for *P. pastoris*; and 4) the high production levels and efficient secretion of recombinant HGH that surprisingly characterizes the expression system described for the first time in this invention, the biotechnological development described here offers important technological and economic advantages for recombinant HGH production.

DISCLOSURE OF THE INVENTION

According to the present invention, the HGH polypeptide can be produced by methylotrophic yeast cells whose genome contains at least one copy of the cDNA sequence encoding HGH functionally associated with the DNA sequence encoding the *S. cerevisiae* alpha factor pre-pro sequence (including the proteolytic processing site: lys-arg) and under the regulation of a promoter region of a methylotrophic yeast gene that can be induced with methanol.

The polypeptide product produced according to the present invention is secreted into the culture medium in a high concentration; furthermore, the expression system invented led to excellent results due to the fact that the *S. cerevisiae* alpha factor pre-pro sequence works adequately to lead the HGH secretion in methylotrophic yeast. The term "DNA sequence encoding functionally operable HGH" used in this description, includes the following hGH cDNA-encoded HGH 22k Da polypeptide precursor (SEQ ID NO:1).

```
Met ala thr gly ser arg thr ser leu leu leu ala phe gly leu leu cys leu pro trp
    -25               -20                  -15                 -10 leu gln glu gly ser ala phe pro thr ile pro leu ser arg leu phe asp asn ala met
    -5                1                5                    10 leu arg ala his arg leu his gln leu ala phe asp thr tyr gln glu phe glu glu ala
15                  20                  25                  30 tyr ile pro lys glu gln lys tyr ser phe leu gln asn pro gln thr ser leu cys phe
35                  40                  45                  50 ser glu ser ile pro thr pro ser asn arg glu glu thr gln gln lys ser asn leu glu
55                  60                  65                  70 leu leu arg ile ser leu leu leu ile gln ser trp leu glu pro val gln phe leu arg
75                  80                  85                  90 ser val phe ala asn ser leu val tyr gly ala ser asp ser asn val tyr asp leu leu
95                  100                 105                 110 lys asp leu glu glu gly ile gln thr leu met gly arg leu glu asp gly ser pro arg
115                 120                 125                 130 thr gly gln ile phe lys gln thr tyr ser lys phe asp thr asn ser his asn asp asp
135                 140                 145                 150 ala leu leu lys asn tyr gly leu leu tyr cys phe arg lys asp met asp lys val glu
155                 160                 165                 170 thr phe leu arg ile val gln cys arg ser val glu gly ser cys gly phe
175                 180                 185                 190 191
```

This sequence is known in the previous art and can be obtained by reverse transcription of messenger RNA (mRNA) to obtain complementary DNA (cDNA) of HGH and converting it enzymatically into a double cDNA chain. The HGH DNA sequence required can also be removed, for example, with restriction enzymes from known vectors harboring the gene sequence of the HGH cDNA; an example of said vectors and ways in which they can be prepared can be taken from several publications including Goeddel (1979), Gray et al., (1985), Becker and Hsiung (1986), Chang et al., (1987), Kato et al., (1987), Hsiung et al. (1989), Ortiz-López (1992) and Pavlakis et al. (1991).

The nucleotide sequence encoding mature HGH to be used in preference, according to this invention, can be found underlined below. The letters in bold and capitals show the Xba I site, created by site directed mutagenesis, and the small letters in bold show the natural Sma I site at the 3' untraslated region of the hGH mRNA (SEQ ID NO:2).

that can be induced with methanol, the cDNA sequence encoding HGH, the DNA sequence encoding the *S. cerevisiae* alpha factor pre-pro sequence, including the DNA sequence of the proteolytic processing site: lys-arg (also referred to as the lys-arg coding sequence) and a transcription terminator functional in methylotrophic yeasts.

```
ATGGCTACAGGCTCCCGGACGTCCCTGCTCCTGGCTTTTGGCCTGCTCTGCCTGCCCTGG    60

CTTCAAGAGGGCAGTGCCTTCCCAACCATTCCCTTATCTAGACTTTTTGACAACGCTATG   120

CTCCGCGCCCATCGTCTGCACCAGCTGGCCTTTGACACCTACCAGGAGTTTGAAGAAGCC   180

TATATCCCAAAGGAACAGAAGTATTCATTCCTGCAGAACCCCCAGACCTCCCTCTGTTTC   240

TCAGAGTCTATTCCGACACCCTCCAACAGGGAGGAAACACAACAGAAATCCAACCTAGAG   300

CTGCTCCGCATCTCCCTGCTGCTCATCCAGTCGTGGCTGGAGCCCGTGCAGTTCCTCAGG   360

AGTGTCTTCGCCAACAGCCTGGTGTACGGCGCCTCTGACAGCAACGTCTATGACCTCCTA   420

AAGGACCTAGAGGAAGGCATCCAAACGCTGATGGGGAGGCTGGAAGATGGCAGCCCCCGG   480

ACTGGGCAGATCTTCAAGCAGACCTACAGCAAGTTCGACACAAACTCACACAACGATGAC   540

GCACTACTCAAGAACTACGGGCTGCTCTACTGCTTCAGGAAGGACATGGACAAGGTCGAG   600

ACATTCCTGCGCATCGTGCAGTGCCGCTCTGTGGAGGGCAGCTGTGGCTTCTAGctgccc   660 ggg                                                           663
```

The yeast species included for use in the present invention are methylotrophic species, which can grow in media containing methanol or other substrates as other carbon sources.

Four genera can be found among the species with the biochemical routes necessary for the use of methanol: Candida, Hansenula, Pichia and Torulopsis.

In the present invention, the yeast specie preferred for use in practice of this invention is *Pichia pastoris*, a strain of yeast known at the industrial level that can use methanol efficiently as the sole source of carbon and energy.

There are several genes that can be induced by methanol in methylotrophic yeasts whose expression is controlled by a regulatory region (also referred as promoter) inducible by methanol. Any of these promoters that can be induced with methanol are suitable for use in the practice of this invention. Examples of these specific regulatory regions include the following *P. pastoris* promoters: alcohol oxidase I (AOXI) gene promoter, alcohol oxidase II (AOX2) gene promoter, dihydroxyacetone synthetase (DAS) gene promoter, promoter of the P40 gene, catalase gene promoter and other similar promoters.

The promoter region to be preferably used to lead the cDNA expression encoding HGH is derived from the *P. pastoris* alcohol oxidase gene inducible with methanol. This yeast is known to have two functional alcohol oxidase genes: alcohol oxidase I (AOX1) and alcohol oxidase II (AOX2). The coding regions of the two AOX genes are closely homologous, their restriction maps are alike and their amino acid sequence are very similar. The proteins expressed by the two genes have similar enzymatic properties, but the AOX1 gene promoter is more efficient with respect to its regulating function and renders higher levels of the gene product than the AOX2 gene promoter; its use is therefore preferred for HGH expression. The AOX1 gene, including its promoter, has been isolated and characterized by Ekkus et al. (1985) and reported in U.S. Pat. No. 4,855,231.

The expression cassette used to transform methylotrophic yeast cells contains: the methylotrophic yeast gene promoter The *S. cerevisiae* alpha-mating factor is a polypeptide with 13 residues, secreted by alpha-mating type cells (Thorner et al., 1981). The pre-pro alpha factor is a leader sequence contained in the precursor molecule of the alpha-mating factor that includes the lys-arg sequence which is necessary for proteolytic processing and secretion (Goeddel, 1991).

According to the present invention, the transcription terminator functional in the methylotrophic yeast used contains both (a) a subsegment encoding the polyadenylation signal and the polyadenylation site in the transcript and/or (b) a subsegment that provides a transcription termination signal for the transcription from the promoter used in the expression cassette. The term "expression cassette", used here and throughout the disclosure of this invention and claims, refers to the DNA sequence that includes functional sequences for both the expression and secretion processes. The complete transcription terminator is taken from a gene encoding a protein that can be the same as or different from the gene that is the source of the promoter.

In order to put this invention into practice, multicopies of the cassette described above should preferably be contained in a DNA fragment with a head-tail orientation. These can be constructed with procedures already known in the state of the technique (Cregg et al., 1993).

According to the present invention, the DNA fragment also includes a selection marker gene. To this purpose any functional selection marker gene from methylotrophic yeast can be used; i.e. any gene that confers a different phenotype on a methylotrophic yeast cell and therefore permits it to be identified and grown in a selective way different from the majority of non-transformed cells. Appropriate selection marker genes include, for example, selection marker systems composed of an auxotrophic mutant of *P. pastoris* strains and a wild type biosynthetic gene that complements the defect in the host cells. For example, for the transformation of *P. pastoris* His4-strains, the HIS4 gene of *S. cerevisiae* or *P. pastoris* can be used, or for the transformation of Arg4-mutants, the ARG4 gene from *S. cerevisiae* and *P. pastoris* can be used.

Furthermore, according to the present invention, the DNA fragment can contain selection marker genes functional in bacteria. Thus, it is possible to use any gene that confers a phenotype in bacteria that makes it possible to transform them for the purposes of identification and selective cultivation or identifying them from most of the non-transformed cells. This additional selection marker permits that the DNA of the invention to be introduced into bacteria such as *E. coli* for their amplification. Appropriate selection marker genes include: the ampicillin (Amp$^r$) resistance gene, the tetracycline (Tc$^r$) resistance gene, and alike.

When the introduction of the DNA from this invention through bacterial cells is contemplated, a bacterial origin of replication should be included in the construction of the DNA in order to ensure maintenance of the DNA of the invention in the bacteria from generation to generation. Examples of bacterial replication sources include: F1, colicin, col E1 and alike.

If the host yeast is transformed with a linear DNA fragment containing the cDNA encoding HGH and the *S. cerevisiae* alpha factor pre-pro sequence (necessary for its, processing and secretion) under the regulation of a *P. pastoris* promoter gene, and if the expression cassette is integrated into the host genome by one of the genetic recombination techniques known in the state of the technique [such as gene replacement by homologous, recombination through a simple crossing over event or by insertion (Rothstein, 1983; and Cregg, 1987)], then the linear DNA fragment is directed towards the desired locus, and the target gene is interrupted in its reading frame, due principally to the fact that the DNA sequences ends of the foreing DNA fragment have sufficient homology with the target gene to allow integration of the DNA fragment into said gene. The interruption of the gene reading frame by one event is usually applicable, provided that the DNA introduced has at least 0.2 kb of homology with the locus fragment at the target gene; however, it is preferable to optimize the degree of homology in order to improve efficiency.

If, according to this invention, the DNA fragment is contained in an expression vector, for example, a circular plasmid, one or more copies of the plasmid can be integrated into the same or different loci by additional events of homologous recombination into the interrupted site in the genome. Linearization of the plasmid with restriction enzymes facilitates this type of integration.

The DNA fragment related to the invention can be used to transform methylotrophic yeast cells as a linearized fragment whose ends contain DNA sequences that have sufficient homology with the target gene to be able to carry out the integration of said DNA fragment within the yeast genome. In this case, integration takes place by replacement of the DNA in the target site by the DNA of the natural gene. Alternatively, the DNA fragment can form part of a circular plasmid that can be linearized to facilitate integration, and will integrate into host chromosome by means of the sequences in the plasmid homologous to those in the yeast genome.

The term expression vector, as used herein, is understood to include vectors that can express the DNA sequences contained in them, where said sequences are functionally associated with other sequences capable to affect their expression, as for example, promoter sequences. In general, expression vectors normally used in recombinant DNA technologies are in the form of "plasmids", circular double-strand DNAs, which in their form as vectors are not joined to the chromosome. In this description, the terms "vector" and "plasmid" are used indistinctly, however, in the embodiments of the present invention it is understood that other types of expression vectors that may be functionally equivalent can be included.

In the DNA fragment of this invention, the functionally associated expression cassette segments indicates that the DNA sequence encoding the HGH polypeptide is functionally placed and oriented with respect to the promoter, the DNA sequence encoding the *S. cerevisiae* alpha factor pre-pro sequence (including the DNA sequences encoding the processing site: lys-arg) and the transcription terminator. Thus, the polypeptide encoding segment is transcribed under the regulation of the promoter into a transcript capable of providing the desired polypeptide after translation has taken place. Due to the presence of the alpha factor pre-pro sequence, the product of the expressed cDNA of HGH is found secreted into the culture medium. An appropriate reading frame and the orientation of the expression cassette segments are within the knowledge of ordinary persons familiar with the state of the technique; additional details of the construction of said cassette are given in the examples.

The DNA fragment provided in this invention can include sequences that permit its replication and selection in bacteria; in this way, large amounts of the DNA fragment can be produced by replication in bacteria.

Methods for the transformation of methylotrophic yeast, such as *Pichia pastoris*, as well as the applicable methods for the cultivation of methylotrophic yeast cells containing a gene. encoding a heterologous protein in their genome are currently known in the previous art.

According to this invention, the expression cassette can be used to transform methylotrophic yeast cells by the spheroplast technique (Cregg, et al., 1985), by eletroporation (Simon and McEntee, 1990) and by the transformation system of lithium chloride (Ito et al., 1984). However, for the purpose of this invention the electroporation and spheroplast methods are preferred.

Positive transformed cells can be characterized by the Polymerase Chain Reaction (PCR) or by "Southern blot" analysis to corroborate the integration of the DNA fragment. In order to analyze the expression of the HGH cDNA inducible with methanol, reverse transcription can be used together with PCR or "Northern blot" technique; and in order to analyze the product, by the presence of HGH secreted into the culture medium upon induction with methanol, electrophoretic or immunological techniques can be used.

Transformed strains that possess the phenotype or genotype desired are grown in fermentors for large scale production of the recombinant product. Batch fermentation in three stages is normally preferred for the fermantation protocol which is already known in the previous art (Clare, et al., 1991; and Brierley, et al., 1991).

The term "culture" means cell propagation in a medium that leads to their growth and all the consequent subcultures. The term "subculture" refers to cultures of cells grown from cells of other cultures (source culture) or any subculture of the source culture, depending on the number of subcultures that have been developed between the subculture of interest and the source culture.

According to the preferred embodiments referred to in this invention, the heterologous protein expression system used for the expression of HGH cDNA uses the promoter derived from the *P. pastoris* AOX1 methanol regulatable gene of *P. pastoris*, which is very efficiently expressed and accurately regulated. This gene can also be the source of the transcription termination sequence. The expression cassette preferred in this invention consists of the following elements, all functionally associated with one another: the *P. pastoris* AOX1 promoter, the DNA sequence encoding the alpha factor pre-pro sequence (including the processing site: lys-arg), the sequence encoding mature HGH and a transcription terminator derived from the *P. pastoris* AOX1 gene, preferably two or more of the expression cassettes mentioned made up of a DNA fragment, in head to tail orientation, in order to generate a multiple expression cassette on one sole DNA fragment. In this invention preference is given to host cells transformed with the expression cassette of which *P. pastoris* is preferred; there shall be at least one mutation that can be complemented with a selectable marker gene present in the transforming DNA fragment. The auxotrophic mutant strain of *P. pastoris* His4(GS 115, ATCC20864) or ARG4(GS 190) is preferred. The fragment containing the expression cassette is inserted into a plasmid containing a marker gene which complements the defective host and can optionally contain additional sequences such as selectable marker genes for bacteria and yeast gene sequences that direct vector integration.

For the development of *P. pastoris* Mut strains (Mut refers to the phenotype that uses methanol), the DNA that consists of the expression cassette for transforming yeast is preferably integrated into the yeast genome by a recombination replacement technique. The expression vector is digested with an appropriate enzyme to produce a linear DNA fragment whose ends are homologous to the AOX1 locus. As a result of the gene replacement, Mut strains are obtained. In Mut strains, the AOX 1 gene is replaced by the expression cassette and therefore the ability to use methanol in this strain is decreased. A slow speed of growth is maintained with methanol due to the expression of the AOX2 gene product. The transformed cells that have integrated the expression cassette into the AOX1 locus (through site-directed recombination) can be identified in a first screening by the presence of the complementator gene. This is preferably detected by the growth of cells in media that lack the complementator gene product and identifying those cells that can grow thanks to the expression of this gene. Furthermore, the selected cells are screened for their Mut genotype by growing them in the presence of methanol and recording the speed of growth or by using PCR.

In the development of Mut+ strains that express HGH cDNA, a fragment containing one or more expression cassettes is preferably integrated into the genome of the host by transforming the host with a circular or linear plasmid containing the cassette. The integration is by addition to a locus (or loci) that has homology with one or more sequences present in the transformating vector.

Transformed methylotrophic yeast that are identified by the desired genotype and phenotype are grown in fermentors. The use of three stage production processes as described above is preferred. The levels of HGH secreted into the medium can be determined by a Western blot analysis, radio-immune-assay or ELISA in the medium and in parallel with HGH standards using antiHGH anti-sera. Electrophoretic analysis or HPLC, after an appropriate previous treatment to the medium, can also be performed. The invention will now be disclosed in more detail with reference to the following non limiting examples.

According to the present invention, a DNA fragment has been constructed containing at least one copy of an expression cassette containing the following DNA sequences in the direction of the transcription reading frame:

i) a promoter region of a methylotrophic yeast gene that can be induced with methanol;

ii) a DNA sequence encoding for:
  a) the *S. cerevisiae* alpha factor pre-pro sequence including the proteolytic processing site: lys-arg;
  b) the polypeptide of 191 amino acids corresponding to the mature human growth hormone; and
  c) a portion of synthetic adapter DNA that replaces parts of (a) and (b) and makes it possible to reconstruct these sequences, ensuring their optimum integration and functionality;

iii) a transcription termination sequence functional in methylotrophic yeast, wherein the DNA sequences are functionally associated with one another in order to carry out the transcription of the sequences encoding the polypeptide of (ii)(b).

According to another section of this invention, an expression vector was constructed containing at least one copy of the expression cassette as described above.

According to another aspect of the present invention, new strains of methylotrophic yeast have been provided particularly the strain with micro-organism deposit certificate No. ATCC 74398, deposited at the American Type Culture Collection, Manassas, Va., on Oct. 22, 1996, containing in their genome at least one copy of the DNA fragment described above.

Viable cultures of methylotrophic yeast cells that can produce recombinant HGH also come within the sphere of this invention.

It will be understood that HGH polypeptides deficient in one or more residues of the amino acid sequence reported in the literature present in HGH in its natural form, or polypeptides containing additional amino acids or polypeptides in which one or more amino acids from the amino acid sequence of HGH in its natural form are replaced by other amino acids, are contemplated within the scope of this invention, as for example all the allelic and non allelic variations genetically related to HGH such as HGHs originating in the placenta, other HGH isoforms (such as the 20 kDa) and GHs of other animal species with similar nucleotide sequences and biological functions; as well as the derivatives specified above or others obtained from simple modifications of the amino acid sequence of natural HGH through site directed mutagenesis or other standard procedures including protein engineering. Types of HGH produced by proteolysis in the host cells that exhibit biological activity similar to mature HGH are also included in the present invention.

EXAMPLES

Example 1

Construction of the Plasmid pPIC9hGH22K

Figure 1:
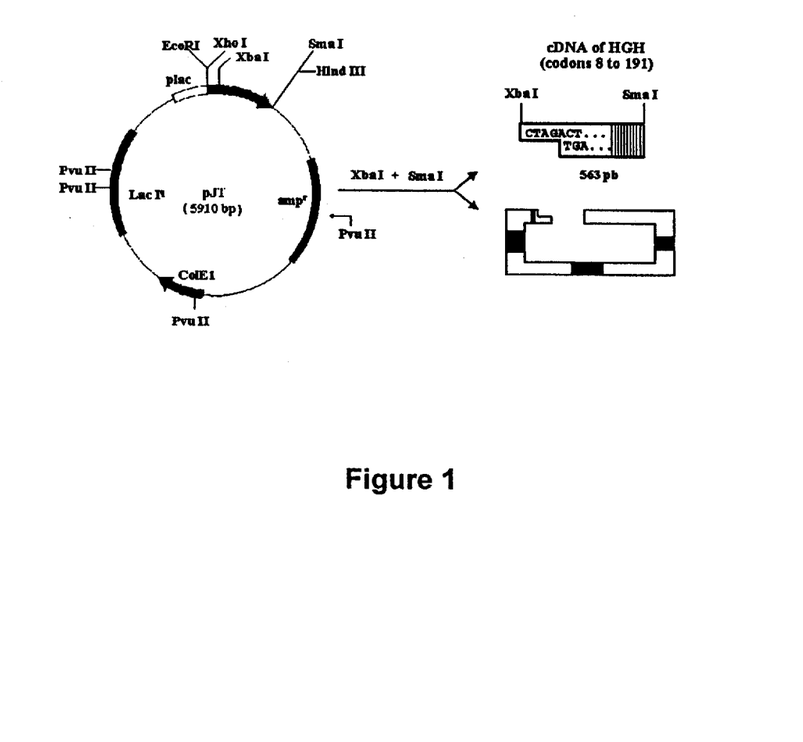
FIG. 1 is a schematic representation of the preparative cut of the pJT vector. It presents the structure of pJT with its most important elements and the products (linkers are SEQ ID NOs:6 and 7) obtained after digestion with enzymes Xba I and Sma I.

The construction of the expression vector described in this invention is carried out as follows:

The Xba I-Sma I fragment of 563 bp is isolated from the vector pJT shown in FIG. 1 which contains a version modified by site directed mutagenesis of the cDNA sequence encoding the human growth hormone hGHc DNA. The 563 bp fragment carries codons 8 to 191 of the mature HGH and also contains a termination codon and 9 nucleotides of the 3' untranslatable region up to the natural Sma1 site.

Figure 2:
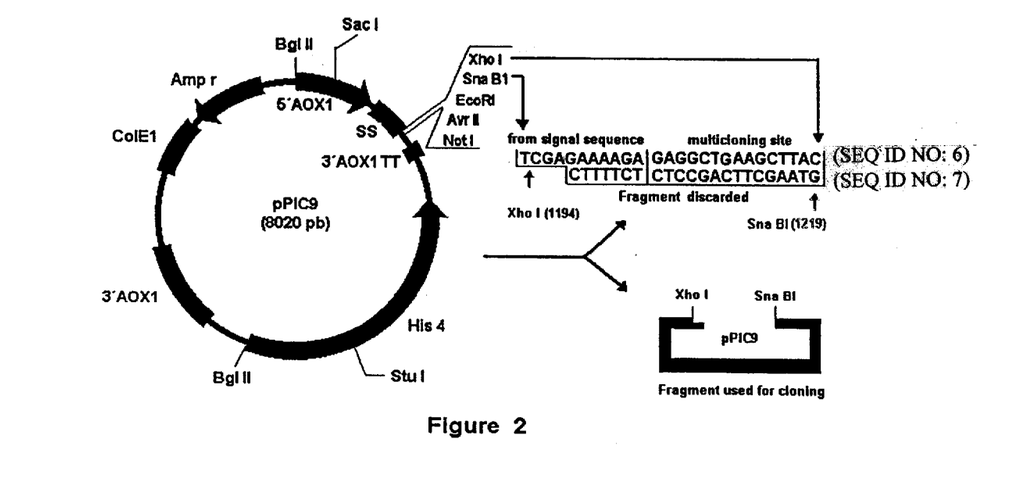
FIG. 2 is a schematic representation of the preparative cut of the pPIC9 expression vector of *Pichia pastoris*. The structure of pPIC9 is represented with its most important elements and the products obtained after digestion with the endonucleases Xho I and Sna BI SEQ ID NOS:6 and 7.

The *Pichia pastoris* expression vector pPIC9, shown in FIG. 2, described in published American Pat. Nos. 4,882,279; 4,855,231 and 4,808,537, is cut with enzymes Xho I and Sna BI. Said expression vector contains the AOX1 gene promoter region located in nucleotide 763, followed by the coding sequence of the *S. cerevisiae* alpha factor pre-pro sequence from nucleotide 949 to 1218 [this sequence contains the lys-arg proteolytic processing site in nucleotide 1201 to 1203 and the glu-ala recognition site (1204–1206), which in turn is followed by the multiple cloning site (1192–241)], an AOX1 transcription termination sequence (1253–1586), an a termination codon at the 3' end of the transcription termination sequence of the AOX1 gene (1246). The pPIC9 vector treated with Xba I and Sna BI (1193–1218) looses 11 nucleotides (1193–1203) from the 3' end of the DNA encoding the *S. cerevisiae* alpha factor pre-pro sequences up to the lys-arg proteolytic processing site. In order to replenish these 11 nucleotides removed from the alpha factor signal sequence and complete the first 7 codons missing from the 5' end of the DNA segment encoding the mature human growth hormone, a synthetic DNA fragment acting as adapter was used (FIG. 3) which includes extremes Xho I and Xba I to facilitate the union of the previously mentioned fragments.

The plasmid pPIC9 digested with Xho I and Sma BI, the 563 bp fragment obtained from the pJT, and the synthetic adapter were put in the same ligating reaction. Subsequently with an aliquot from the ligating reaction, *E. coli* cells were transformed for propagation and for the subsequent analysis of the clones in order to detect plasmid pPIC9hGH22k carriers.

a) Preparation of the Plasmids pPIC9 and pJT.

*E. coli* TOP 10F' calcium-competent cells (Invitrogen, Co. San Diego, Calif., USA) were transformed with the plasmids pPIC9 and PJT. The preparation of calcium-competent bacteria and the transformation were carried out in accordance with the protocols described by Sambrook and colleagues (1989). Subsequently, colonies of bacteria carrying plasmid pPIC9 or pJT were taken and grown in 1L of LB broth (1% Tryptone, 0.5% Sodium Chloride and 1% Dextrose) in order to then isolate plasmid DNA by the large scale method based on gentle lysis with TRITON X-100 followed by ultracentrifugation in cesium a chloride density gradient (Cab-Barrera and Barrera-Saldaña, 1988). In this way, a source of good quality plasmids was obtained with which to construct the plasmid pPIC9hGH22k.

b) Preparation of Fragments for Ligation and the Ligating Reaction.

The digestion of pJT with enzyme Xba I was performed with the following mixture of 50 μL of reaction: 2 μL of Xba I (10/μL), 5 μL of 10×buffer solution, 5 μL of 10×bovine serum albumin (BSA), 13 μL of DNA (pJT at 600 ng/μL), add 25 μL MILLI-Q water (purified water from a MILLI-Q water system, obtained from Millipore).

The digestion of pPIC9 with the endonuclease Xho I and Sna BI was carried out in the following way: first the digestion was made with the enzyme Sna BI incubating at 37° C. for 5 hours with the following reaction mixture: 5 μL of Sna BI (4 U/μL), 5 μL of 10×buffer, 5 μL 10×BSA, 15 μL DNA (pPIC9 800ng/μL) and 20 μL MILLI-Q water (purified water from a MILLI-Q water system, obtained from Millipore). Subsequently 2 μL of the endonuclease Xho I (10 U/μL) were added and the resulting mixture was incubated overnight at 37° C.

The success of the digestions was verified by analysing 1 μL aliquots by means of electrophoresis on a 1% agarose gel. Once the above mentioned preparative digestions had finished, preparative electrophoresis was carried out on a 1% agarose gel with 25 μL of each digestion reaction and staining was performed with ethidium bromide 2 μg/mL in TBE (Tris-Boric Acid-EDTA buffer). The 563 bp fragments from the digestion of pJT with Xba I and Sma I and the 7966 bp fragment from the digestion of pPIC9 with Xbo I and Sna BI were recovered from the gel by cutting the corresponding bands with the aid of a surgical knife. The fragments were extracted from the agarose matrix using the "GENECLEAN" technique (The GENECLEAN II Kit Bio 101, Inc., Calif., USA) and were stored in a TE buffer (10 m Tris-HCl, 1 mm EDTA, pH=8) at −20° C. until required. The synthetic adapter used was constructed from complementary synthetic oligonucleotides that were generated in an OLIGO-1 000 synthesizer (Beckman Inc., Fullerton, Calif., USA). Prior to the ligation reaction, these fragments were annealed by means of their complementarity of bases in the following way: a mixture containing: 5 μL of 10×TE buffer, 3.3 μL of 150 mM NaCl, 21 μL of oligonucleotide 1 (0.74 mM) and 21 μL of the oligonucleotide 2 (0.70M), giving rise to a solution of 10 mM NaCl, 10 mM Tris-HCl and 1 mM EDTA, was prepared. The mixture was heated at 80° C. for 5 minutes, left to cool slowly until it reached room temperature and stored at −20° C. until required.

c) Analysis of the pPIC9hGH22K Carrier Clones.

Twenty of the colonies obtained from the transformation (ampillicin resistant) were taken up for individual inoculation in tubes with 4 mL of LB broth with ampicillin (100 mg/L). They were incubated at 37° C. and 250 rpm for 18 hours. Subsequently, 2 mL of each culture was taken and plasmid DNA was isolated on a small scale (mini preparation), in accordance with the alkaline method described by Sambrook and colleagues (1989). The plasmid DNA isolated in each of the clones was treated with the endonuclease Xba I in order to detect plasmid pPIC9hGH22K which should present specific 7210 and 1377 bp fragments, since said enzyme cuts in positions 1222 and 2599. Electrophoresis was performed on a 0.8% agarose gel in order to analyze the digestions. The clones that showed the expected pattern were characterized more exhaustively performing digestion with each of the following endonucleases: Xho I, Xho I+Eco RI, Xba I, Pvu II and Bgl U. According to the computer analysis fed with the plasmid sequence pPIC9hGH22K, the theoretical fragments are as follows: Xho I=8587 bp; Xho I +Eco RI=7990 and 597 bp; Xba I=7210 and 1377 bp; Pvu II=4875, 2948, 497 and 267 bp; and Bgl II=4574, 2403 and 1616 bp.

One of the clones that showed the expected restriction pattern was selected and a plasmid DNA preparation was made on a large scale (Cab-Barrera and Barrera-Saldaña, 1988). In this way, a source of good quality plasmids was obtained with which to perform the transformation of *Pichia pastoris*.

Three hundred colonies were obtained from the transformation of *E. coli* with 5 μL of the ligating product, twenty of which were taken to determine if they carried recombinant plasmid (pPIC9hGH22K). Three of them turned out to have the plasmid that generated the specific fragments expected when digested with endonuclease Xba I (7210 and 1377 bp). The characterization of plasmid DNA from one of the chosen clones, with endonucleases Xho I, Xho I+Eco RI, Xba I, and Pvu II, +Bgl II, showed that the size of the fragments obtained for each digestion, observed in electrophoretic analysis on an agarose gel, corresponded to the expected sizes in accordance with their restriction map.

Example 2

*Pichia pastoris* Transformation

Once the identity of the vector pPIC9hGH22K had been ensured, digestions were carried out to linearize the plasmid with either endonucleases Sac I or Stu I and in this way perform the transformation. The plasmid linearized with Sac I favors gene insertion in the AOX1 locus and the plasmid linearized with Stu I gene insertion in locus His4 (Invitrogen, 1994), thus developing Mut+ strains in both cases. The *Pichia pastoris* GS 115 cells (ATCC20864) were transformed by electroporation (Simon and McEntee, 1990) with the linearized plasmid as follows: *Pichia pastoris* cells were grown in 50 mL of YPD broth at 30° C. and 250 rpm until a late logarithmic phase (OD600 2.0) was reached. The cell mixture was then centrifuged at 5000 rpm for 5 minutes (centrifuge IEC CENTRA MP4R Rotor 854) in order to obtain the cell package which was washed twice, first in 25 mL of sterile MILLI-Q water (purified water from a MILLI-Q water system, obtained from Millipore) and then with 2 mL of 1M sterile sorbitol, and was resuspended in 0.5 mL of the latter ($OD_{6000}$=2.0). 20 μL of this cell suspension was mixed with 5 μL of linear DNA (50ng/μL), and was transferred to 0.15 cm electroporation micro-chambers. Electroporation was performed with a pulse of 400V, 10F and a field of force of 2666.6V/cm. 10 μL of the electroporation mixture was taken and 0.5 μL of sterile 1M sorbitol was added. Subsequently, the content of the Eppendorf tube was spread on plates with a minimum dextrose medium DM (1.34% yeast nitrogen base (YNB), 4×10–5% biotin, 1% dextrose) and incubated at 30° C. until the colonies appeared (3–6 days). Since the DM medium does not have histidine, only yeasts that have integrated the plasmid into their genome and that therefore are able to synthesize histidine (his+) grow. Subsequently, colonies were taken from both preparations and conserved for subsequent analysis.

The transformation of *Pichia pastoris* with the two linearized plasmids resulted in 54 clones transformed with the plasmid cut with Sac I and 33 clones transformed with the plasmid cut with Stu I. The clones obtained presented an His+ phenotype (capable of synthesizing histidine), due to having grown in a medium without histidine, which was acquired by integration of the plasmid.

The clones resulting from the transformation with both preparations (digestions with SacI and Stu I) were grown in tubes with 4 mL of YPD broth (1% yeast extract, 2% peptone, 2% dextrose) for 48 hours at 30° C. and with agitation at 250 rpm. Subsequently, a cell pellet was, obtained through centrifugation at 16000 g (14000 rpm Eppendorf 5402 centrifuge) for 5 minutes, it was resuspended in YPD with 15% glycerol in such a volume that an $OD_{600}$ of 50 to 100 was reached, it was rapidly frozen in $N_2$ liquid and stored at −70° C. (Izquierdo, 1993).

Example 3

Analysis of the Genomic DNA of the Transformant a) Preparation of Genomic DNA

In order to extract genomic DNA from *P. pastoris*, a modification of the TSNT technique was used M. Izquierdo, 1993). The yeasts were grown in 4 mL of YPD broth for 24 to 48 hours, the cell package was harvested by means of centrifugation for 5 minutes at 16000 g and was washed with 500 μL of MILLI-Q water (purified water from a MILLI-Q water system, obtained from Millipore). 300 μL of TSNT solution (2% TRITON X-100 (an octylphenylpolyethylene alcohol with 100 ethylene oxide units), 1% SDS, 100 mM NaCl, 10 mM Tis-HCl and 1 mM EDTA, pH=8) and 650 μL of saturated phenol were added to the cell package and it was mixed in a vortex for 10 seconds. Subsequently, 150 μL of Sevag (chloroform; isomylic alcohol 1:1) were added and it was agitated for 5 minutes. Once the agitation had finished, 300 μL of TE pH=8 was added to the mixture which was centrifuged for 10 min at 16000 g. The aqueous phase was transferred to a 2 mL microcentrifuge tube and the DNA was precipitated adding 1.3 mL of 100% ethanol. The resulting mixture was centrifuged for 10 min at 16000 g and the supernatant was decanted. The DNA pellet was resuspended in 500 μL of TE and 3 μL of RNAse A (10 mg/mL) were added, incubating at 37° C. for 15 min. Two phenol-Sevag extractions were performed, and the aqueous phase was separated by centrifugation for 5 min and 16000 g. 10 μL of ammonium acetate 7.5M and 1.3 mL of 100% ethanol were added in order to precipitate the DNA, the resulting mixture was mixed by inversion and centrifuged for 10 min at 16000 g to decant the supernatant. The pellet was washed twice with 70% ethanol and resuspended in 50 μL of TE, a solution which was spectrophotometrically measured in order to quantify the DNA and determine the quality parameter ($A_{260}/A_{280}$). Electrophoresis was also carried out on a 0.8% agarose gel in TBE and ethidium bromide dye in order to see whether the genomic DNAs were degraded or not.

b) Polymerase Chain Reaction (PCR)

The genomic DNAs from six clones were analyzed by PCR to corroborate the identify of the plasmid pPIC9hGH22K as well as its integration in the genome of *P. pastoris*. The 5'(5'-GACTGGTTCCAATGACAAGC-3') primer (SEQ ID NO:3) anneals in the 5'AOX1 region (nucleotides 855–875) of plasmid pPIC9, while the 3'(5'GCAATGGATTCTGACATCC-3') (SEQ ID NO:4) does so in the 3'AOX1 TT region (nucleotides 1327–1347) of the same. Since the PCR of the plasmid pPIC9 results in an amplified product of 449 bp and the multicloning site (MCS; where the heterologous gene is inserted) of pPC9 is between the two annealing regions of the PCR primers, the cloned fragment causes a 567 bp increase in the size of the amplified product, generating a 1016 bp fragment for pPIC9hGH22K. The PCR of the genomic non-recombinant DNA of *P. pastoris* results in a 2200 bp product coming from the amplification of the AOX1 gene. The PCR of the genomic DNA of the clones (recombinant *P. pastoris*) that conserves the AOX1 gene (Mut+) results in products 2200 and 1016 bp long corresponding to the AOX1 gene and the integration cassette, respectively.

PCR standardization was carried out in order to obtain clear bands, as far as possible from saturation, in order to detect multi-copies of the expression cassette should there be any. Different concentrations of DNA substrate and primers were used for the standardization and the number of cycles was also varied. The standardized PCR had the following conditions: 1×PCR buffer (Promega), 2 ng/μL of genomic DNA, 200M dNTP's, 0.5M of primer 5'AOX1, 0.5M of primer 3'AOX1, sterile water and 2.5 units of Taq polymerase in a 25 μL reaction. A PTC-150 (MJ Research Inc., Watertown, Mass., USA) thermocycler was used. The program carried out was the following: one initial denaturation step of the cycle at 94° C. (2 min.), 18 cycles consisting as an denaturation at 94° C. (1 min.), annealing at 60° C. (1 min.) and extension at 72° C. (1 min.) and a final extension step at 72° C. (7 min.). An analysis of 5 μL of the PCR product was performed by electrophoresis on a 0.8% agarose gel in TBE.

As Mut+ clones always have a sole copy of the AOX1 gene, the intensity relation between the amplified bands (2200 bp and 1016 bp) is the same in different clones that contain one sole copy of the integrated plasmid. Considering that most (approximately 99%) of the *P. pastoris* clones would have a copy of the integrated plasmid, they have the same intensity relation between their amplified bands. Clones with multicopies of the integrated plasmid would therefore be easy to detect since they could be distinguished from the majority of clones with one sole copy when the intensity relation between both bands (2200 bp/1016 bp) is changed due to an increase in the intensity of the 1016 bp ethidium recombinant band. A densitometric analysis was therefore carried out of the PCR bands stained with ethidium bromide in order to determine the existence of clones with multicopies of the integrated plasmid or if there were only single-copy clones.

Figure 3:
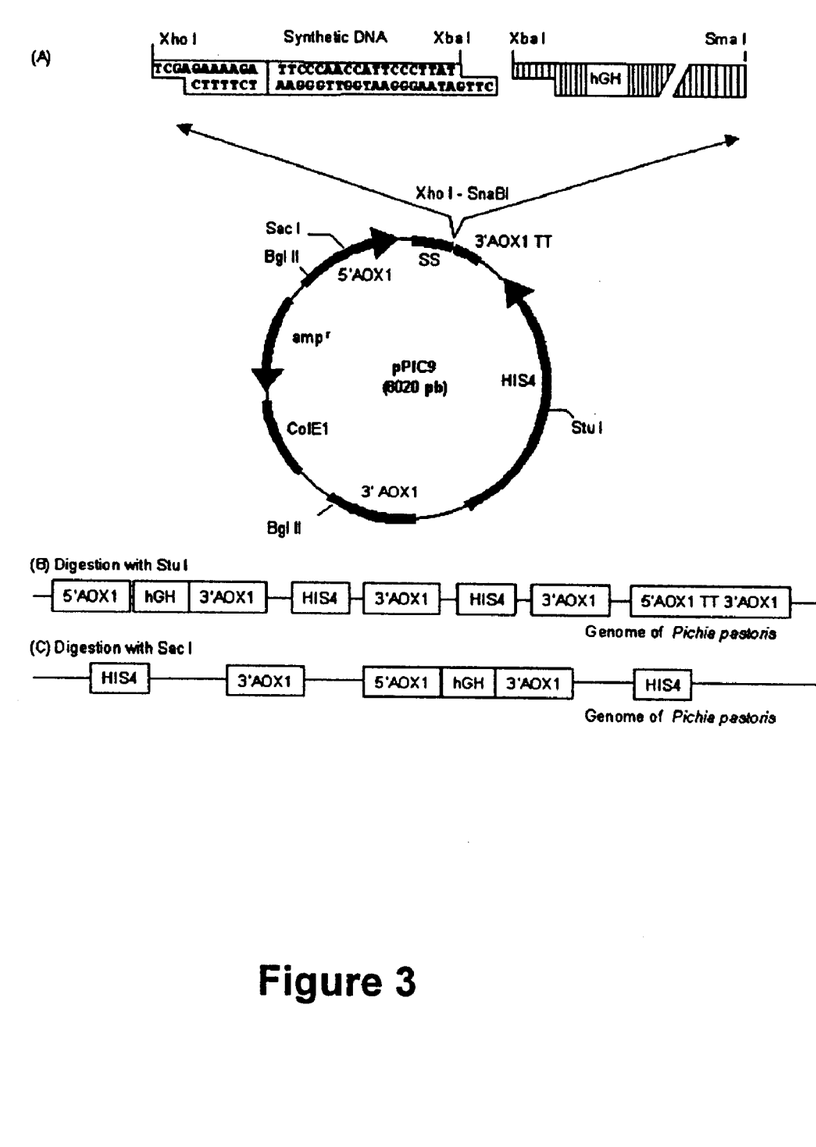
FIG. 3 is the structure of the pPIC9hGH22K expression plasmid (linkers are SEQ ID NOS:8 and 9). The pPIC9hGH22k (A) plasmid that contains the sequence encoding mature HGH at sites XhoI-Sna BI SEQ ID NOS: 6 and 7 between the AOX1 promoter (5' AOX1) and terminator (AOX1-t). The two types of chromosome integration obtained are: (B) integration of the vector in HiS4, (C) integration of the vector in AOX1.

The size of each of the amplified products obtained by PCR corresponded to the expected sizes for each of the DNA substrates used: pP1C9 (449 bp), pPIC9hGH22K (1016 bp), non-recombinant *P. pastoris* genomic DNA (2200 bp) an Mut+ recombinant clones of *P. pastoris* (1016 and 2200 bp). FIG. 3 shows each of the amplified products, separated by electrophoresis on an agarose gel and stained with ethidium bromide. Lane M shows the molecular weight marker (lambda DNA digested with, EcoRI+Hindll), lane A shows the amplified pPIC9 product, in lane B the amplified pPIC9hGH22K product can be found, lane C; shows the amplified product of *P. pastoris* non-recombinant genomic DNA, lanes 1 to 6 represent amplified products from different *P. pastoris* Mut+ recombinant clones. The flourescence ratio between the 2200 bp and 1016 bp bands are also shown for each recombinant clone with a mean of 0.996±0.041 (X±E.S.,n=6), which shows that each of these clones has one sole copy of the integrated expression cassette.

Example 4

HGH Production from Recombinant *P. pastoris* Clones a) Fermentations

Four clones prepared as in examples 1 to 3 were selected for each of the transformations (DNA digested with Sac I and Stu I). Each of the clones were inoculated from the conservation medium (vials with 15% glycerol at −70° C) onto plates with YPD agarose (1% yeast extract, 2% peptone and 2% dextrose), streaking in three fields in order to obtain isolated colonies. As previously mentioned, the fermentations with recombinant *P. pastoris* are divided into two phases: the cell growth phase and the induction or recombinant protein production phase. Using isolated colonies, four 250 mL Erlenmeyer flasks with 25 mL of buffered medium and glycerol [BMG, 100 mM dibasic potassium phosphate, pH=6, 1.34% yeast nitrogen base (YNB), $4\times10^{-5}$% biotin, 1% glycerol) were inoculated, incubated at 30° C. and agitated at 250 rpm until reaching an $OD_{600}$ of 4.0. 22 mL BMG medium contained in a 250 mL Erlenmeyer flask were inoculated with 3.125 mL of this propagated culture to reach an initial $OD_{600}$ of 0.5, it was incubated in the same conditions until it reached an $OD_{600}$ of 1.0. Subsequently, the BMG medium was eliminated by centrifuigation (5000 rpm 5 min., IEC CENTRA MP4R centrifuge, rotor 854) and was resuspended in 25 mL of buffered medium with methanol [BMM, 100 mM dibasic potassium phosphate, pH=6, 1.34% yeast nitrogen base (YNB), $4\times10^{-5}$% biotin, 0.5% methanol]. The incubation was continued at 30° C. and 250 rpm for 150 h and in this way the induction or recombinant protein production stage began. 125 μL of methanol were added every 24 h to compensate loss through evaporation. Subsequently, SDS-PAGE and immunodetection by the Western blot technique were performed on recombinant HGH from the culture medium free of cells to corroborate its identity.

b) Protein Analysis (Protein Determination, SDS-PAGE and Densitometry)

Since in this system, rHGH is secreted into the culture medium, an analysis was performed of the proteins from the culture medium which was dialyzed against MILLI-Q water (purified water from a MILLI-Q water system, obtained from Millipore) beforehand. The dialysis bags with 25 mL of medium were kept in a beaker container with 4L of cold water for 1.5 h, with moderate agitation and the MILLI-Q water (purified water from a MILLI-Q water system, obtained from Millipore) was changed twice more. The dialyzed medium was concentrated in the following way: four volumes of a methanol:acetone solution (1:1) were added, it was left overnight at −20° C., centrifuged for 10 min at 10,000 rpm (IEC CENTRA MP4R centrifuge, rotor 854), the supernatural was removed and the protein package was vacuum dried. The package was resuspended in ⅟20 of its original in volume in SDS-PAGE buffer, it was heated for 10 min at 100° C., centrifuged for 5 seconds in order to lower the liquid that had evaporated and condensed on the tube walls. 10–20 μL were applied for electrophoresis on polyacrylamide gel. Protein separation was performed by electrophoresis in a discontinuous 12% polyacrylamide [4% staking gel and 12% resolving gel under denaturing conditions (SDS-PAGE)]. An initial voltage of 80V was applied until coloring indicator penetrated approximately 1 cm into the staking gel and then was increased to 140V. Electrophoresis was maintained until the coloring indicator reached the resolving gel and was finally increased to 180V. The gel was fixed in a fixing solution (50% methanol, 10% acetic acid, in deionized water) with agitation at 40 rpm for 1 h. This fixing solution was replaced by a staining solution (0.5% Coomassie brilliant blue, 50% methanol and, 10% acetic acid, in deionised water) and incubation continued with agitation for 25 min. Then the coloring solution was withdrawn and a decoloring solution was added to the gel (5% methanol, 7% acetic acid, in deionized water) which was agitated at 40 rpm for 1 h. The gel continued to lose color with periodic changes of the decoloring solution until blue bands of protein were observed against a clear background of the gel.

The relative percentage of the recombinant HGH band with respect to all other bands in each lane of the gel where total culture media proteins were resolved was determined by densitometry. The equipment used was a Zeineh Soft Laser densitometer (Scanning Sensitometer, Model SLR-2D/1D, Biomed Instruments, Inc.) with Zeineh Programs Universal Software (Advanced American Biotechnology Biomed VGA Programs).

Protein determination was carried out by the Bradford method (Martinez, 1993). A spectrophotometer was used to determine the absorbance at 595 nm presented by bright Coomassie blue bound to the evaluated proteins. Calibration curves were made with bovine serum albumin standards (BSA, Sigma Chemical., Co. St Louis, Md., USA) in a concentration interval of 1 to 6 μg/mL. Both the samples and the standards were prepared in triplicate.

c) Immunodetection by "Western Blot"

An SDS-PAGE analysis was carried out under the conditions described in the preceding section. Subsequently, electrotransference was carried out to a nitrocellulose membrane (0.45 microns Bio-Rad) for 3 h at 100V which was then incubated for 1 h with agitation at 40 rpm in a blocking solution (0.3% TWEEN 20 (polyoxyethylene sorbitan monolaurate) and 0.3% bovine serum albumin in PBS) in order to block the protein-free areas of the membrane.

As the first antibody, an anti-HGH antiserum developed in the rabbit (Sigma) was used in a dilution of 1:1000 in 1% of the blocking solution in PBS. Incubation was overnight at 4° C. Subsequently three 15 min. washings were performed at moderate agitation with 0.3% TWEEN 20 (polyoxyethylene sorbitan monolaurate) in PBS. As the second antibody a rabbit anti-IgG developed in the goat (Sigma) was used in a dilution of 1:1000 in a 1% blocking solution in PBS. It was incubated for 1 h at room temperature and washed three times for 15 min with moderate agitation with 0.3% TWEEN 20 (polyoxyethylene sorbitan monolaurate) in PBS. 10 mL of the mixture of chromogenic substrates that contained 66 μL of 5% nitro blue tetrazolium (NBT) and 33 μL of 5% 5-bromo-4-chloro-3-indophosphate (BCIP) in an alkaline phosphate buffer (100 mM NaCl, 5 mM $MgCl_2$, 100 mM Tris-HCl, pH=9.5) were used for color development. The resulting mixture was added to the membrane and moderately agitated until the bands of interest appeared (approximately 10 min).

The four recombinant clones that were analyzed for the characterization of the product of the integrated heterologous gene expression produced and secreted recombinant HGH. The electrophoretic analysis on the polyacrylamide gel of the culture medium of a fermentation with one of the *P. pastoris* clones showed that in the culture medium of the induced cells a band of approximately 22k Da appears corresponding to recombinant HGH, while in the non-induced cell culture medium, there was no band. The immunoidentity of recombinant HGH was also shown through by the Western blot technique, using anti-HGH antibodies.

d) Protein Sequencing

In order to carry out the analysis of the amino terminal end of HGHr the dialyzed culture medium an induced fermentation of the recombinant *P. pastoris* strain (clone 19) was resolved by SDS-PAGE and transferred to a nitrocellulose filter. The band corresponding to a 22kDa protein that had been immunoreactive to anti-HGH antibodies in prior assays was cut and the 15 amino acid residues at the amino terminal end were sequenced. Automated sequencing was carried out in an automatic protein sequencer using the Edman technique. Subsequently, the PTH derivatives were separated for their identification. The sequence of the 15 amino acid residues from the amino terminal end of recombinant HGH secreted by clone 19 was identical to the native HGH sequence. This implies the correct recognition of the processing site for the *S. cerevisiae* alpha factor pre-pro sequence.

e) Adipogenic Activity

A colony was inoculated in 3 mL of BMG medium in 25 mL tubes. The cells grew at 30° C. with agitation at 250 rpm until the culture reached an $OD_{600}$ of between 2 and 6. Subsequently, the cell package was obtained by centrifugation at 10000 rpm (IEC CENTRA MP4R centrifuge, rotor 854) for 5 min, the supernatant was removed and it was resuspended in a BMM medium (inductor medium) in a volume that produced an $OD_{600}$ of 1.0. 3 mL of the adjusted medium were transferred to sterile tubes and incubated at 30° C. for 150 h to induce heterologous hGH gene expression. In order to maintain the induction, 100% methanol was added every 24 h to a final concentration of 0.5%. Subsequently, centrifugation was performed at 10,000 rpm (IEC CENTRA MP4R centrifuge, rotor 854) in order to separate the cell pellet from the culture medium and to carry out an analysis of the proteins in the culture medium. Total proteins of the 24 transformed clones were determined and the percentage of recombinant HGH by densitometry of gels of 7 of the transformed clones with the highest levels of total proteins was calculated. With the values obtained from these parameters the concentration reached was calculated in mg of rHGH/L of the culture medium.

Example 5

Recombinant High Production

Twenty-four transformed colonies were analyzed (18 Sac I cuts and 6 Stu I cuts) in order to select the transformant with the highest levels of recombinant HGH production using preliminary culture conditions.

A colony was inoculated in 3 mL of BMG medium in 25 mL tubes. The cells grew at 30° C.: with agitation at 250 rpm until the culture reached an $OD_{600}$ of between 2 and 6. Subsequently, the cell package was obtained by centrifugation at 10000 rpm (IEC Centra MP4R centrifuge, rotor 854) for 5 min, the supernatant was removed and it was resuspended in a BMM medium (inductor medium) in a volume that produced an ODES of 1.0. 3 mL of the adjusted medium were transferred to sterile tubes and incubated at 30° C. for 150 h to induce heterologous hGH) gene expression. In order to maintain the induction, 100% methanol was added every 24 h to a final concentration of 0.5%. Subsequently, centrifugation was performed at 10,000 rpm (IEC Centra MP4R centrifuge, rotor 854) in order to separate the cell pellet from the culture medium and to carry out an analysis of the proteins in the culture medium. Total proteins of the 24 transformed clones were determined and the percentage of recombinant HGH by densitometry of gels of 7 of the transformed clones with the highest levels of total proteins was calculated. With the values obtained from these parameters the concentration reached was calculated in mg of rHGH/L of the culture medium.

Total protein concentration of the culture medium of the 24 clones analyzed varies between 3 to 11 mg/L. The indirect estimation of percentage of recombinant HGH obtained by densitometry of polyacrylamide gels of the 7 clones with the greatest levels of proteins varied from 35 to 80%. The production of recombinant HGH (mg/L) in these 7 clones had values of 3 to 9 mg of recombinant HGH/L of culture medium. The clone that reached the highest levels of recombinant HGH production (9 mg/L) was the one used to carry out production at flask level.

Example 6

Scaling Up Recombinant High Production with *Pichia pastoris*

This stage consisted of producing recombinant HGH with a selected recombinant *P. pastoris* clone.

The *P. pastoris* strain that produced the highest levels of rHGH (80% and 9 mg/L) in assay tubes was used for rHGH production. In this stage of rHGH extracellular production a total of 7 tests were performed modifying the production variables:

concentration of methanol (inductor) in culture medium (%)

optic density at the beginning of induction ($OD_{600}$)

induction time (IT)

The production indicator was HGH concentration in the culture medium which was obtained from the parameters evaluated (% of rHGH and the concentration of total proteins mg/L). In this way, the result obtained was expressed in mg of recombinant HGH/L of culture medium. The factors used for the production, as well as the percentage values of rHGH, total proteins and levels of rHGH production were analyzed employing the simplex sequencial method.

In the table below, the variation of the factors with respect to the assays performed can be seen to show that the requirement of methanol concentration increased during production, while $OD_{600}$ and IT showed oscillating values. OD600 fluctuated between 0.91 and 1.43, them methanol concentration between 0.25 and 1.36%, the IT between 140 and 186 h.

| ASSAY | % M | $OD_{600}$ | IT (h) | TP (mg/L) | % of HGHr | HGH (mg/L) |
|---|---|---|---|---|---|---|
| STAEI | | | | | | |
| A | 0.25 | 1.43 | 140 | 4.9 | 27.3 | 1.3 |
| B | 0.251 | 1.10 | 175 | 10.8 | 64.1 | 6.9 |
| C | 0.75 | 1.08 | 140 | 16.5 | 76.2 | 12.6 |
| D | 0.75 | 1.38 | 175 | 15.9 | 82.2 | 13.1 |
| STAEII | | | | | | |
| C1 | 0.75 | 0.94 | 140 | 16.2 | 78.9 | 12.8 |
| E | 0.92 | 0.91 | 186 | 14.0 | 76.6 | 10.8 |
| STAEIII | | | | | | |
| E1 | 0.92 | 0.97 | 186 | 12.1 | 68.9 | 8.4 |
| F | 1.36 | 1.07 | 160 | 18.6 | 48.6 | 9.1 |
| STAEV | | | | | | |
| C2 | 0.75 | 1.26 | 140 | 13.8 | 55.7 | 7.7 |
| G | 1.06 | 1.37 | 166 | 7.7 | 31.1 | 2.4 |

M = methanol, OD = optic density, IT = induction time, TP = total proteins

Similarly, the relative percentage (estimated indirectly by densitometry) of rHGH fluctuated between 31 and 82% showing oscillating values, while the concentration of total proteins fluctuated between 4.9 and 18.6 mg/L and showed an increase during production, although in the last assay a decrease was observed. rHGH production fluctuated between 1.3 and 13 showing an increase and then a decrease. Assay (D) provided to be the best as can be seen in the table. It presented a total protein concentration of 15±0.6mg/L (X±E.S., n=3) with a percentage of 80.7% (indirect measurement) that can be translated into rHGH production of 12.3±0.7 (X±E.S., n=3) and was 900% more productive than the assay with the least production (A). Therefore determining conditions to reach optimum levels of rHGH production were: $OD_{600}$: 1.38, methanol concentration: 0.75% and IT: 175 h.

Having described the present invention, it is considered to be a novelty and therefore the content of the following claims is claimed as property.

What is claimed is:

1. An isolated DNA molecule containing one or more copies of an expression cassette that includes:
   (i) an alcohol oxidase promoter of a methylotrophic *Pichia pastoris* gene that can be induced with methanol;
   (ii) a DNA sequence encoding:
      (a) a *S. cerevisiae* alpha factor pre-pro signal sequence including the proteolytic processing site lys-arg;
      (b) a 191 amino acid polypeptide of mature human growth hormone (HGH); and
      (c) a synthetic adapter DNA for optimum integration and functionality; and
   (iii) a transcription termination sequence functional in *Pichia pastoris*, where:
   the DNA sequence encoding the alpha factor pre-pro sequence and the DNA sequence encoding the HGH polypeptide are functionally associated in such a way that under a process of transcription and translation, biologically active mature HGH polypeptide is secreted into a culture medium; and
   wherein the promoter and termination sequence are functionally associated with the DNA sequence encoding the HGH polypeptide, and
   the promoter directs the transcription of the DNA sequence encoding the HGH polypeptide by induction with methanol in *Pichia pastoris*.

2. The DNA molecule of claim 1 that further contains at least one selection marker gene and one replication origin for bacteria.

3. The DNA molecule of claim 1 in which the promoter regions is selected from the group of promoters regions inducible with methanol from *Pichia pastoris* consisting of the alcohol oxidase I (AOX1) gene promoter and the alcohol oxidase II (AOX2) gene promoter.

4. The DNA molecule of claim 1, in which the DNA sequence encodes the mature HGH polypeptide having the sequence of SEQ ID NO:5.

5. A plasmid that contains the DNA molecule of claim 4.

6. A *Pichia pastoris* yeast cell transformed by homologous recombination with the DNA molecule of claim 1 or the plasmid of claim 5.

7. The transformed *Pichia pastoris* yeast cells of claim 6, wherein the promoter and the termination sequence are from the *P. pastoris* AOX1 gene.

8. The transformed *Pichia pastoris* yeast cell of claim 7, wherein said DNA molecule integrates by homologous recombination into a *Pichia pastoris* which uses methanol as a sole carbon source.

9. The transformed *Pichia pastoris* yeast cell of claim 8 containing multiple copies of the expression cassette.

10. A viable culture of *P. pastoris* cell containing the cell of claim 6.

11. A process for the production of human growth hormone, comprising culturing the *Pichia pastoris* cell culture of claim 10 under conditions wherein the HGH polypeptide is expressed and secreted into the culture medium.

12. The process of claim 11 wherein the culture is grown in a medium containing methanol as a sole carbon source.

13. The process of claim 11 wherein the culture has a Mut+ phenotype.

14. The process of claim 11 wherein the culture has a Mut phenotype.

15. The process of claim 11, wherein the concentration of HGH in the culture medium is 1.3–13.1 mg/L.

16. The process of claim 11, wherein the concentration of HGH in the culture medium is 13 mg/L.

17. The process of claim 11, wherein the relative percentage of HGH secreted into the culture medium is between 31–82% of the total protein.

18. The process of claim 11, wherein the relative percentage of HGH secreted into the culture medium is 82% of the total protein.

19. The process of claim 11, wherein the culture is induced, and the culture has, at the beginning of induction an $OD_{600}$ of 1.38, and also at the beginning of the induction the concentration of methanol in the culture medium is 0.75%, and the induction time is 175 hours.

20. A *Pichia pastoris* cell transformed with the DNA molecule of claim 1.

21. The transformed *Pichia pastoris* yeast cell of claim 20, comprising multiple copies of the expression cassette.

22. The transformed *P. pastoris* yeast cell of claim 21 wherein the multiple copies of the expression cassette are oriented in a head to tail orientation.

23. A *Pichia pastoris* cell transformed with the DNA molecule of claim 1 which is a cell of microorganism deposit No. ATCC 74398.

24. A viable *P. pastoris* cell culture containing the cell of claim 23.

* * * * *

SEQUENCE LISTING

<160> NUMBER OF SEQ ID NOS: 9

<210> SEQ ID NO 1
<211> LENGTH: 217
<212> TYPE: PRT
<213> ORGANISM: Homo sapiens

<400> SEQUENCE: 1

```
Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr Ile Pro Leu
                20                  25                  30

Ser Arg Leu Phe Asp Asn Ala Met Leu Arg Ala His Arg Leu His Gln
            35                  40                  45

Leu Ala Phe Asp Thr Tyr Gln Glu Phe Glu Glu Ala Tyr Ile Pro Lys
        50                  55                  60

Glu Gln Lys Tyr Ser Phe Leu Gln Asn Pro Gln Thr Ser Leu Cys Phe
 65                 70                  75                  80

Ser Glu Ser Ile Pro Thr Pro Ser Asn Arg Glu Glu Thr Gln Gln Lys
                85                  90                  95

Ser Asn Leu Glu Leu Leu Arg Ile Ser Leu Leu Leu Ile Gln Ser Trp
           100                 105                 110

Leu Glu Pro Val Gln Phe Leu Arg Ser Val Phe Ala Asn Ser Leu Val
       115                 120                 125

Tyr Gly Ala Ser Asp Ser Asn Val Tyr Asp Leu Leu Lys Asp Leu Glu
   130                 135                 140

Glu Gly Ile Gln Thr Leu Met Gly Arg Leu Glu Asp Gly Ser Pro Arg
```

```
                145                 150                 155                 160
Thr Gly Gln Ile Phe Lys Gln Thr Tyr Ser Lys Phe Asp Thr Asn Ser
                    165                 170                 175

His Asn Asp Asp Ala Leu Leu Lys Asn Tyr Gly Leu Leu Tyr Cys Phe
            180                 185                 190

Arg Lys Asp Met Asp Lys Val Glu Thr Phe Leu Arg Ile Val Gln Cys
        195                 200                 205

Arg Ser Val Glu Gly Ser Cys Gly Phe
    210                 215

<210> SEQ ID NO 2
<211> LENGTH: 663
<212> TYPE: DNA
<213> ORGANISM: Artificial Sequence
<220> FEATURE:
<223> OTHER INFORMATION: Description of Artificial Sequence: DNA
      encoding the mature human growth hormone, containing an
      artificial XbaI site introduced by modifying
      nucleotides at positions 21 and 24

<400> SEQUENCE: 2
atggctacag gctcccggac gtccctgctc ctggcttttg gcctgctctg cctgccctgg      60
cttcaagagg gcagtgcctt cccaaccatt cccttatcta gactttttga caacgctatg    120
ctccgcgccc atcgtctgca ccagctggcc tttgacacct accaggagtt tgaagaagcc    180
tatatcccaa aggaacagaa gtattcattc ctgcagaacc cccagacctc cctctgtttc    240
tcagagtcta ttccgacacc tccaacagg gaggaaacac aacagaaatc caacctagag    300
ctgctccgca tctccctgct gctcatccag tcgtggctgg agcccgtgca gttcctcagg    360
agtgtcttcg ccaacagcct ggtgtacggc gcctctgaca gcaacgtcta tgacctccta    420 aaggaccta g aggaaggcat ccaaacgctg atggggaggc tggaagatgg cagccccgg    480 actgggcaga tcttcaagca gacctacagc aagttcgaca caaactcaca caacgatgac    540
gcactactca gaactacgg gctgctctac tgcttcagga aggacatgga caaggtcgag    600
acattcctgc gcatcgtgca gtgccgctct gtggagggca gctgtggctt ctagctgccc    660
ggg                                                                    663

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Linker

<400> SEQUENCE: 3
gactggttcc aattgacaag c                                                 21

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Linker

<400> SEQUENCE: 4
gcaatggatt ctgacatcc                                                    19

<210> SEQ ID NO 5
<211> LENGTH: 191
<212> TYPE: PRT
```

<213> ORGANISM: Homo sapiens

<400> SEQUENCE: 5

```
Phe Pro Thr Ile Pro Leu Ser Arg Leu Phe Asp Asn Ala Met Leu Arg
  1               5                  10                  15

Ala His Arg Leu His Gln Leu Ala Phe Asp Thr Tyr Gln Glu Phe Glu
                 20                  25                  30

Glu Ala Tyr Ile Pro Lys Glu Gln Lys Tyr Ser Phe Leu Gln Asn Pro
             35                  40                  45

Gln Thr Ser Leu Cys Phe Ser Glu Ser Ile Pro Thr Pro Ser Asn Arg
 50                  55                  60

Glu Glu Thr Gln Gln Lys Ser Asn Leu Glu Leu Leu Arg Ile Ser Leu
 65                  70                  75                  80

Leu Leu Ile Gln Ser Trp Leu Glu Pro Val Gln Phe Leu Arg Ser Val
                 85                  90                  95

Phe Ala Asn Ser Leu Val Tyr Gly Ala Ser Asp Ser Asn Val Tyr Asp
                100                 105                 110

Leu Leu Lys Asp Leu Glu Glu Gly Ile Gln Thr Leu Met Gly Arg Leu
            115                 120                 125

Glu Asp Gly Ser Pro Arg Thr Gly Gln Ile Phe Lys Gln Thr Tyr Ser
130                 135                 140

Lys Phe Asp Thr Asn Ser His Asn Asp Asp Ala Leu Leu Lys Asn Tyr
145                 150                 155                 160

Gly Leu Leu Tyr Cys Phe Arg Lys Asp Met Asp Lys Val Glu Thr Phe
                165                 170                 175

Leu Arg Ile Val Gln Cys Arg Ser Val Glu Gly Ser Cys Gly Phe
            180                 185                 190
```

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence:
      Linker (Figure 2)

<400> SEQUENCE: 6
tcgagaaaag agaggctcaa gcttac                                          26

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:
      Linker (Figure 2)

<400> SEQUENCE: 7
cttttctctc cgacttcgaa tg                                              22

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:
      Linker (Figure 3)

<400> SEQUENCE: 8
tcgagaaaag attcccaacc attcccttat                                      30

```
<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Linker
      (Figure 3)

<400> SEQUENCE: 9
cttttctaag ggttggtaag ggaatagttc                                     30
```